United States Patent [19]

Moore

[11] Plant 4,150

[45] Nov. 15, 1977

[54] CHERRY TREE

[75] Inventor: Ralph S. Moore, Visalia, Calif.

[73] Assignee: L. E. Cooke Co., Visalia, Calif.

[21] Appl. No.: 763,107

[22] Filed: Jan. 27, 1977

[51] Int. Cl.[2] ..... A01H 5/03

[52] U.S. Cl. ..... Plt./37

[58] Field of Search ..... Plt./37

*Primary Examiner*—Robert E. Bagwill

[57] ABSTRACT

A sweet cherry variety of the Bing type characterized by its ability to mature fruit in areas of high temperature and low humidity.

1 Drawing Figure

1

The present invention relates to a new and distinct variety of hardy, vigorous, well foliaged and productive cherry tree of the Bing type; the variety being primarily characterized — as to novelty — (A) by its ability to set and mature a satisfactory crop of fruit in areas of higher temperatures and lower humidity, such as the south San Joaquin Valley of California, not usually conducive to cherry culture, the fruit of the present variety being similar to the Bing and Black Tartarian varieties (neither variety patented). And (B) by its abundant production of large dark red fruit of excellent eating quality.

The variety is further characterized by:

Relatively early flowering habit, first blooms opening on Mar. 14th in the 1975 season, being about 5 days later than the Royal Ann variety (not patented). The flowers are borne in quite large clusters on fruiting spurs. Flower buds are medium size; medium length. Color of flowers: white. In the 1975 season the original tree, as well as several younger trees propagated from the original, were in full bloom between Mar. 24th and Mar. 28th.

A tree (plant) which is of vigorous, rather upright growth habit, becoming only medium sized, as compared with Royal Ann (not patented); the foliage and fruit being similar to the Black Tartarian variety.

A tree which grows and fruits satisfactorily even in areas with a warmer, drier climate, thus making this variety useful for planting in areas with similar growing conditions. This variety is especially desirable for home orchard and yard planting.

The present variety of fruiting sweet cherry tree was discovered by me as a chance seedling originating in my own home orchard. The parent variety from which the seed came is unknown.

Subsequent to origination of the variety I successfully budded two young trees in my orchard to this new variety. It has also been successfully reproduced in the test orchard of the L. E. Cooke Co., located at Visalia, Calif., the reproductions having run true in all respects.

The color photograph illustrates the fruit and foliage of the variety.

Referring now specially to the new and distinct variety of fruiting sweet cherry, the following is a detailed description thereof in outline; all major color plate identification being by reference to the British Colour Council Horticultural Colour Chart, except where common terms of color definition are employed.

Type: Hardy, vigorous, seedling, medium size tree, upright.

Class: Fruiting, sweet.

2

Tree: Medium size; vigorous, upright. Very productive; regular bearer.

Trunk: Stocky; relatively smooth — similar to Black Tartarian.

Branches: Stocky; relatively smooth.

*Lenticels.*—Relatively few — small.

Leaves:

*Length.*—5"-6⅝"; width —2½"-2⅞".

*Size.*—Large. Shape; lanceolate, acutely pointed (both base and tip) — thick.

*Color.*—Medium green (darker than Royal Ann). Veining quite pronounced. Numerous fine grayish hairs along midrib and lesser ribs (veins) on reverse (lower) surface of leaf.

*Margin.*—Serrate — average about 7-10 teeth (serrations) per inch of leaf margin.

*Petiole.*—Long 1¾" to 2"; slender.

*Glands.*—Generally 2 — sometimes 1 or none, alternate, oval, reddish. Located at base of blade on petiole.

Flowers: flower buds — size; medium; medium length; obtuse, plump. Flowers abundantly; early (1975 season: started blooming on March 14th — 5 days later than Royal Ann; was in full bloom March 24-28).

Fruit: Specimens described were grown and observed at Visalia, Calif., May 1975.

*Date of ripening.*—First fruit picked — May 16, 1975, firm ripe; about 5 days later than Black Tartarian.

*Date of last picking.*—June 1, 1975.

*Size.*—Large; diameter, axil 13/16" (2 cm); transverse in suture plane 12/16" (about 18-19 mm).

*Form.*—Uniform; globose; broadly conical.

*Suture.*—An inconspicuous line; shows only in basal one half or less.

*Ventral surface.*—Rounded slightly toward base.

*Cavity.*—Flaring at base; gently rounded; circular.

*Depth.*—About 7-8 mm; breadth; about 8-9mm.

*Base.*—Rounded. Apex: rounded. Pistil point: very slightly depressed.

Skin: Medium thick; medium toughness; tenacious to flesh. Tendency to crack: none noted. Color: when fully ripe: nearly Chrysanthemum Crimson 824 or dark Blood Red 00823.

Flesh: color — dark blood red next to skin and seed. Fleshy portion dark red with lighter (whitish) areas throughout (see color illustration). Juice: abundant; rich. Texture: medium firm, meaty. Fibers: few, tender. Ripens: evenly. Flavor: subacid, mild, delicate. Eating quality: best — flavor sweeter and more mild than Black Tartarian or Royal Ann.

Stone: semi-free, clings along suture; free on sides, retains short fibers along suture ridge.

*Size.*—Small; length 7/16" (11 mm); Breadth 6/16" (9 mm); thickness 5/16 (8 mm).

*Form.*— Oval to ovid; base rounded, nearly flat; apex rounded; sides equal, surface quite smooth except along suture edge — rough area about 3/16" or less wide with vertical ridges from base to apex. Color of stone: light gray — brown. Tendency to split: none observed.

Use: Local market; desert, culinary, canning.

Keeping quality: good. Fruit will remain on tree in good condition longer than most comparable cherry varieties, such as Black Tartarian. Specimens of first fruit picked, May 16, 1975, were placed in plastic bag and placed on office desk at room temperature. When bag was opened and fruit examined on June 10th it was still in good edible condition.

Resistance to insects, diseases: no unusual susceptabilities noted.

The cherry tree and its fruit as herein described and illustrated may vary in slight detail due to climatic, soil, and cultural conditions under which the variety may be grown; the present description being of the variety as grown at Visalia, Calif.

The following is claimed:

1. A new and distinct variety of fruiting cherry tree of the Bing type, essentially as described and illustrated, of vigorous, upright growth habit with large dark red fruit similar to the Black Tartarian variety but larger and generally having a sweeter more pleasing flavor; a tree which grows and fruits well in warm dry areas such as the south San Joaquin Valley in California and which bears abundant annual crops; the variety is further characterized by the keeping quality of its fruit, by abundant medium green foliage and ease of propagation by regular nursery methods.

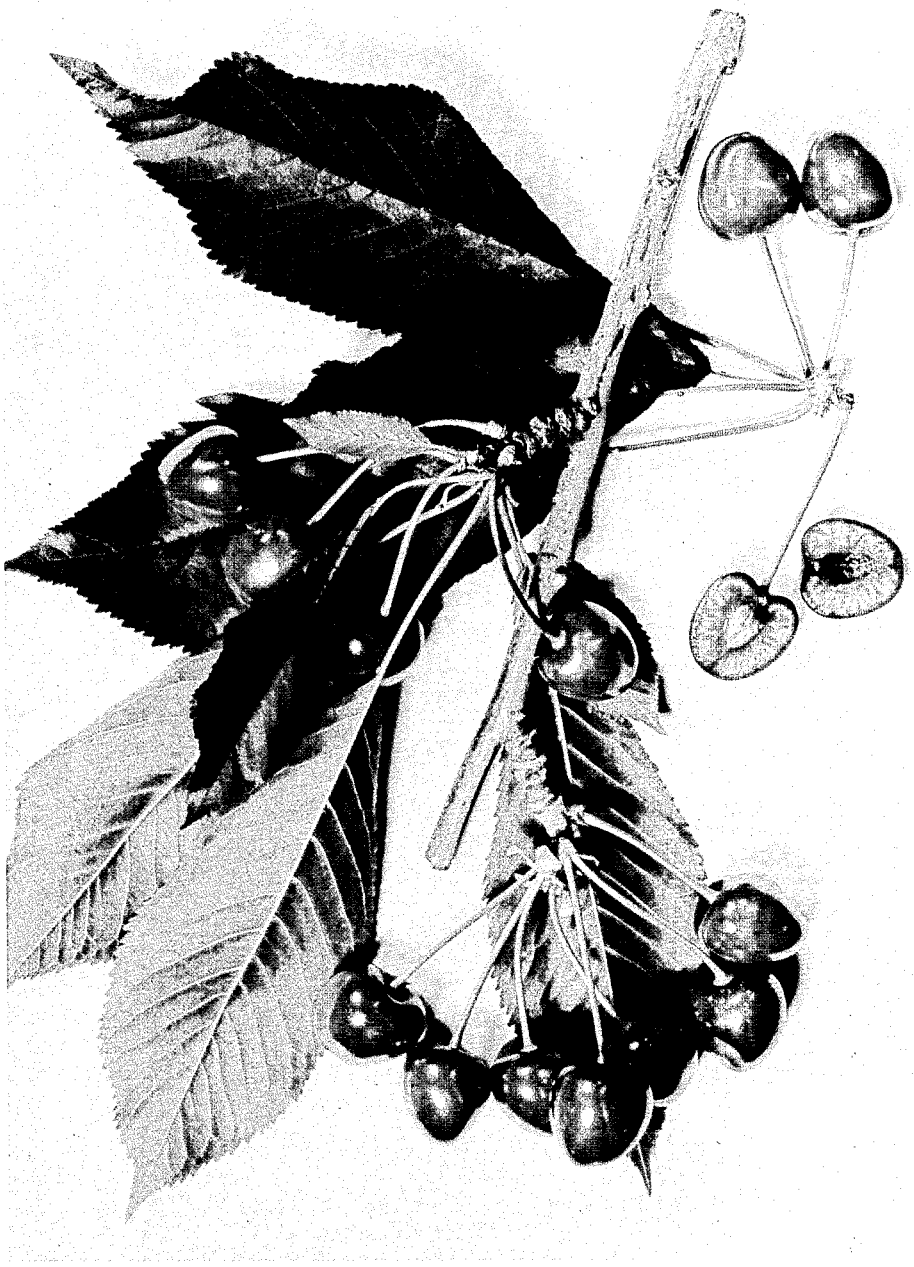

* * * * *